(12) United States Patent
Saini et al.

(10) Patent No.: US 8,632,474 B2
(45) Date of Patent: *Jan. 21, 2014

(54) SYSTEM AND METHOD FOR PROVIDING INFORMATION BASED ON MENSTRUAL DATA

(75) Inventors: Shivani Saini, Kobe (JP); Randy Joseph Peterson, Kobe (KR)

(73) Assignee: The Procter and Gamble Company, Cincinnati, OH (US)

( * ) Notice: Subject to any disclaimer, the term of this patent is extended or adjusted under 35 U.S.C. 154(b) by 505 days.

This patent is subject to a terminal disclaimer.

(21) Appl. No.: 11/529,945

(22) Filed: Sep. 29, 2006

(65) Prior Publication Data

US 2007/0027404 A1   Feb. 1, 2007

Related U.S. Application Data

(63) Continuation of application No. 10/351,131, filed on Jan. 24, 2003, now Pat. No. 7,166,078, which is a continuation of application No. PCT/US00/21833, filed on Aug. 10, 2000.

(51) Int. Cl.
    *A61B 10/00*   (2006.01)

(52) U.S. Cl.
    USPC ........................................................ 600/551

(58) Field of Classification Search
    USPC .............. 600/551, 300, 547, 588, 591, 301; 434/429, 430; 379/106.02; 709/203; 340/5.9; 706/15
    See application file for complete search history.

(56) References Cited

U.S. PATENT DOCUMENTS

| 4,685,471 | A | * | 8/1987 | Regas et al. ................... 600/547 |
| 5,515,344 | A | | 5/1996 | Ng |
| 5,606,535 | A | | 2/1997 | Lynn |
| 5,777,905 | A | | 7/1998 | Dowdle |
| 5,836,890 | A | | 11/1998 | Jackson |
| 5,974,124 | A | * | 10/1999 | Schlueter et al. ........ 379/106.02 |
| 6,018,343 | A | | 1/2000 | Wang |
| 6,093,027 | A | * | 7/2000 | Unger et al. ................... 434/429 |
| 6,368,113 | B1 | * | 4/2002 | Unger et al. ................... 434/429 |
| 6,419,637 | B1 | | 7/2002 | Cheng et al. |
| 7,166,078 | B2 | * | 1/2007 | Saini et al. ..................... 600/551 |
| 2001/0023419 | A1 | * | 9/2001 | Lapointe et al. ................ 706/15 |

FOREIGN PATENT DOCUMENTS

| JP | 10080426 A | 3/1998 |
| JP | 2000116607 A | 4/2000 |
| JP | 2000139857 A | 5/2000 |
| JP | 2000197612 A | 7/2000 |
| WO | WO 0139584 A2 * | 6/2001 |

* cited by examiner

*Primary Examiner* — Brian Szmal
(74) *Attorney, Agent, or Firm* — Megan C. Hymore; Andrew J. Hagerty; Amanda T. Barry

(57) ABSTRACT

A system for delivering information through a computer. The system comprises: data collecting means for collecting personal data including menstrual data regarding a menstrual cycle on a woman from a user; phase identification means for identifying a phase within the menstrual cycle; storage means for storing predetermined information; selection means for selecting information from the storage means, which is personalized based on the phase identified by the phase identification means; and delivery means for delivering the personalized information.

23 Claims, 4 Drawing Sheets

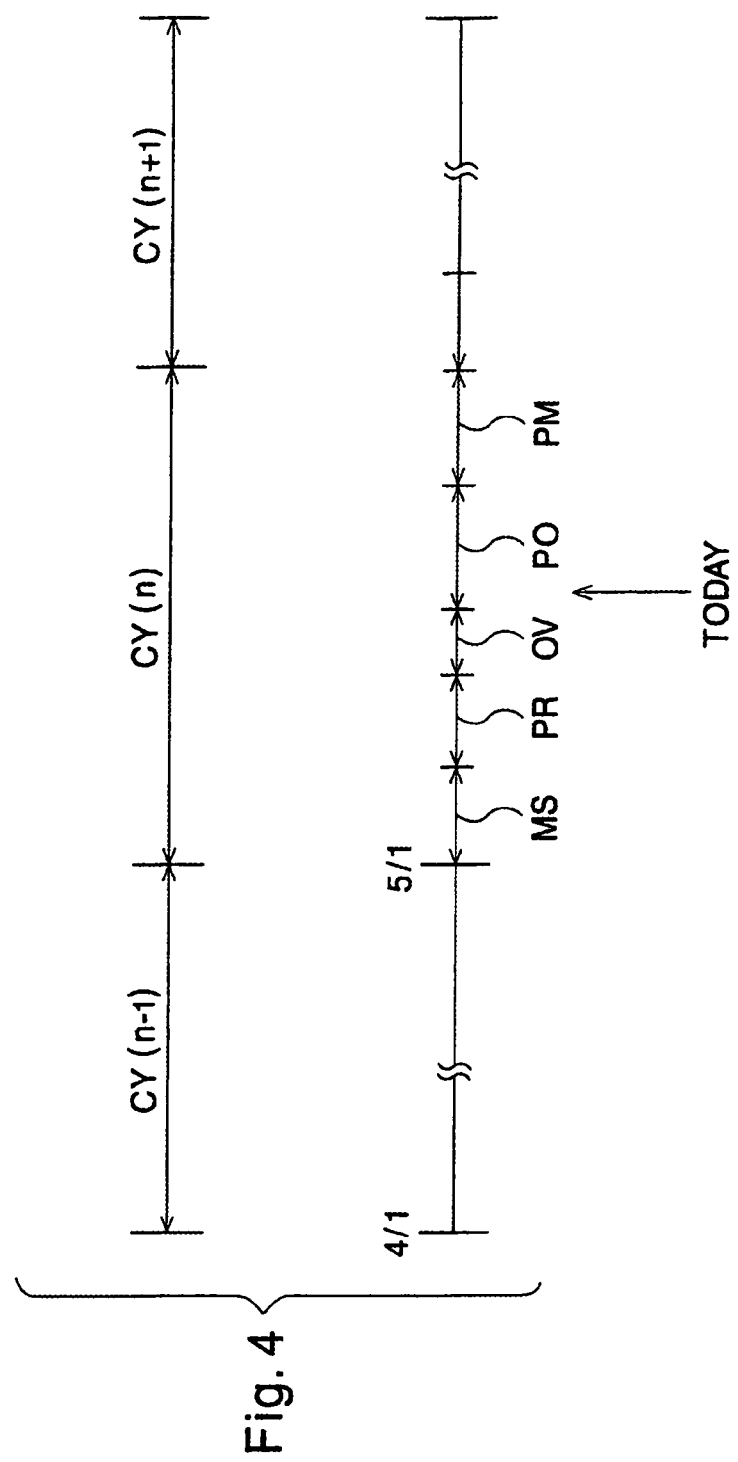

SYSTEM AND METHOD FOR PROVIDING INFORMATION BASED ON MENSTRUAL DATA

CROSS REFERENCE TO RELATED REFERENCES

This application is a continuation of U.S. Ser. No. 10/351,131, filed Jan. 24, 2003, now U.S. Pat. No. 7,166,078, which is a a continuation of International Application PCT/US00/21833 with an International filing date of Aug. 10, 2000.

FIELD OF THE INVENTION

The present invention generally relates to computer based information providing systems, and particularly to a system and method for timely providing personalized, information. The information to be provided is chosen based on personal data including menstrual data collected from a user through a computer network. Examples of such information to be provided include physical information, mental information, activity information, and lifestyle information.

BACKGROUND OF THE INVENTION

The Internet has developed rapidly over the past several years, and is known as a very useful tool for obtaining and/or providing various information. Many people or companies who want to provide certain information have a web site which is accessible by Internet users through the Internet. The Internet users can obtain information by visiting the web site which is chosen by inputting the web site address. For example, consumer product companies have their own web sites which can provide information about their products as well as other information. Consumers can obtain necessary or desired information about their products by accessing to the web site through the Internet.

Those companies generally expect their users to re-visit their web sites repeatedly since it is believed that consumers can obtain appropriate and timely information about their products, thereby resulting in promoting their motivation for re-purchasing products. For example, The Procter & Gamble Company has an Internet web site at an address of http://www.pg.com/. This web site provides information relating to their products such as feminine hygiene products, baby care products, laundry and home care products, hair care products, cosmetic products, and the like.

Feminine hygiene products such as sanitary napkins, pantiliners and tampons are devices that are used by females during their menstrual cycles. These products are designed to absorb or otherwise contain liquid and other discharges from the human body and to prevent body and clothing soiling. It is well known that women who are the users of feminine hygiene products have a menstrual cycle which occurs once for about every 28 days on average. It is also known that physical and mental conditions of a women change day to day during her menstrual cycle. The change of these conditions is very personal or depends on the woman.

Conventionally, a woman typically monitors the numbers of days from the first day from her last menstruation so that she can make a daily, weekly and/or monthly plan for her future activities. It is because her physical and mental conditions change depending on the day in the menstrual cycle, and she wants to choose an appropriate or preferable activity which helps her better manage her cycle and improve the quality of her life.

In 1990, the population of menstruating women was about 60 million women in the US, about 30 million in Japan, and about 1.5 billion in the world. Every 28 days on average, these women (excluding those not menstruating because of pregnancy or other reasons), pass through their menstrual cycles. It is known that the body and mental conditions of a woman change depending on the phases the woman stands during the menstrual cycle. It is also known that the body and mental conditions of a woman is influenced by her hormone levels in her menstrual cycle. Thus, it is preferred that activities during the menstrual cycle are properly managed. Examples of such activities include conception planning, PMS (Pre-Menstrual Syndrome), countermeasures, product purchase planning, health improvement information, and the like. However, normally women are not completely aware of their current phases in their menstrual cycles. Thus, they can not regularly get appropriate information or advice at an appropriate timing. As a result, women tend not to effectively manage their activities appropriately during their menstrual cycles because of lack of information appropriately and timely obtained.

For example, many women experience from PMS which is symptomized by, alteration in mood, interrupted sleep, and lower sex drive. Most women are not aware that this condition is related to their menstrual cycle. Scientific studies have shown that vitamin and mineral deficiencies are associated with PMS symptoms. Specifically, it is said that Vitamin B6, and Calcium supplements can be taken to reduce or avoid the effects of PMS. If a woman is informed of the dates on which she will be experiencing PMS, and receive advise on how to reduce/avoid the effects of PMS, she can better manage her menstrual cycle.

Based on the foregoing, there is a need for a system and method for timely providing, through a computer, valuable information which is personalized based on a woman's menstrual data. There is also a need for a system and method for an Internet web site which can promote people's repeated visits to the web site and/or communication through electronic mails (or e-mails).

SUMMARY OF THE INVENTION

The present invention is directed to a system (or an apparatus) for delivering information through a computer. The system comprises: data collecting means for collecting personal data including menstrual data regarding a menstrual cycle on a woman from a user; and phase identification means for identifying a phase within the menstrual cycle.

In one aspect of the invention, the system further comprises: storage means for storing predetermined information; selection means for selecting information, from the storage means, which is personalized based on the phase identified by the phase identification means; and delivery means for delivering the personalized information.

In another aspect, the system comprises: storage means for storing predetermined information; and delivery means for delivering the predetermined information in response to the phase identified by the phase identification means.

In yet another aspect, the system comprises: generating means for generating information which defines at least a phase of the menstrual cycle; and delivery means for delivering the information.

The present invention is also directed to a method for delivering information through a computer. The method comprises the steps of: collecting personal data including menstrual data regarding a menstrual cycle on a woman from a user; and identifying a phase within the menstrual cycle.

In still another aspect, the method comprises the steps of: selecting information, from the storage means, which is personalized based on the phase identified by the phase identification means; and delivering the personalized information.

In yet another aspect, the method further comprises the steps of: delivering the information stored in storage means in response to the phase identified by the phase identification means.

In still another aspect, the method comprises the steps of: generating information which defines at least a phase of the menstrual cycle; and delivering the information.

The foregoing answers the need for a system and method for timely providing, through a computer, valuable information which is personalized based on a woman's menstrual data. The foregoing also answers the need for a system and method for an Internet web site which can promote people's repeated re-visits.

These and other features, aspects, and advantages of the present invention will become evident to those skilled in the art from reading of the present disclosure.

BRIEF DESCRIPTION OF THE DRAWINGS

While the specification concludes with claims particularly pointing out and distinctly claiming the invention, it is believed that the invention will be better understood from the following description of preferred embodiments taken in conjunction with the accompanying drawings wherein like designations are used to designate substantially identical elements, and in which:

FIG. 4 is a cycle chart of succeeding three menstrual cycles of a woman.

DETAILED DESCRIPTION OF THE INVENTION

Herein, the terms "comprise", "include" and "contain" mean that other element(s) and step(s) which do not affect the end result can be added. These terms encompass the terms "consisting of" and "consisting essentially of".

Herein, the term "feminine hygiene products" refers to disposable absorbent articles used by women for catamenial protection. Such products include sanitary napkins, tampons, interlabial products, incontinence devices, and pantiliners. The term "disposable" is used herein to describe absorbent articles which are not intended to be laundered or otherwise restored or reused as an absorbent article (i.e., they are intended to be discarded after a single use, and, preferably, to be disposed of in an environmentally compatible manner). Herein, the term "absorbent article" refers to devices which absorb and contain body exudates, and, more specifically, refers to devices which are placed within, against, or in proximity to, the body of the wearer to absorb and contain the various exudates discharged from the body.

Herein, the term "user" refers to a person who can access to the information delivery system of the present invention and has an interest in knowing information which is directed by a woman's menstrual data. Typically, the user is same as the woman, however, the user can be a different person from the woman, for example, a woman's husband, a woman's friend, a woman's parent(s), and the like.

Computers have been used for processing and providing data or information for many years. One typical style for usage of such computers is called a "stand alone computer". In general, the stand alone computer is not connected to a computer network and merely provides data or information to a user who directly operates the computer. Another typical style for usage of such computers is called a "server computer". The server computer is connected to a computer network and is accessible from client computers which are located remotely. While the client computers are typically in the form of a desktop computer, the client computers may be laptop computers or can be in the form of a mobile device. The server computer provides data or information in response to a request transferred from a user device which is located remotely. Such request is sent to the sever computer through a computer network. Herein, the term "computer network" refers to a network which includes at least two, and preferably many computers connected through a communication line. Preferred examples of the computer network include a Local Area Network (LAN), the Internet, and variations on the Internet such as a Wireless Access Protocol (WAP) network and a mobile phone network (e.g., i-mode®).

Figure 1:
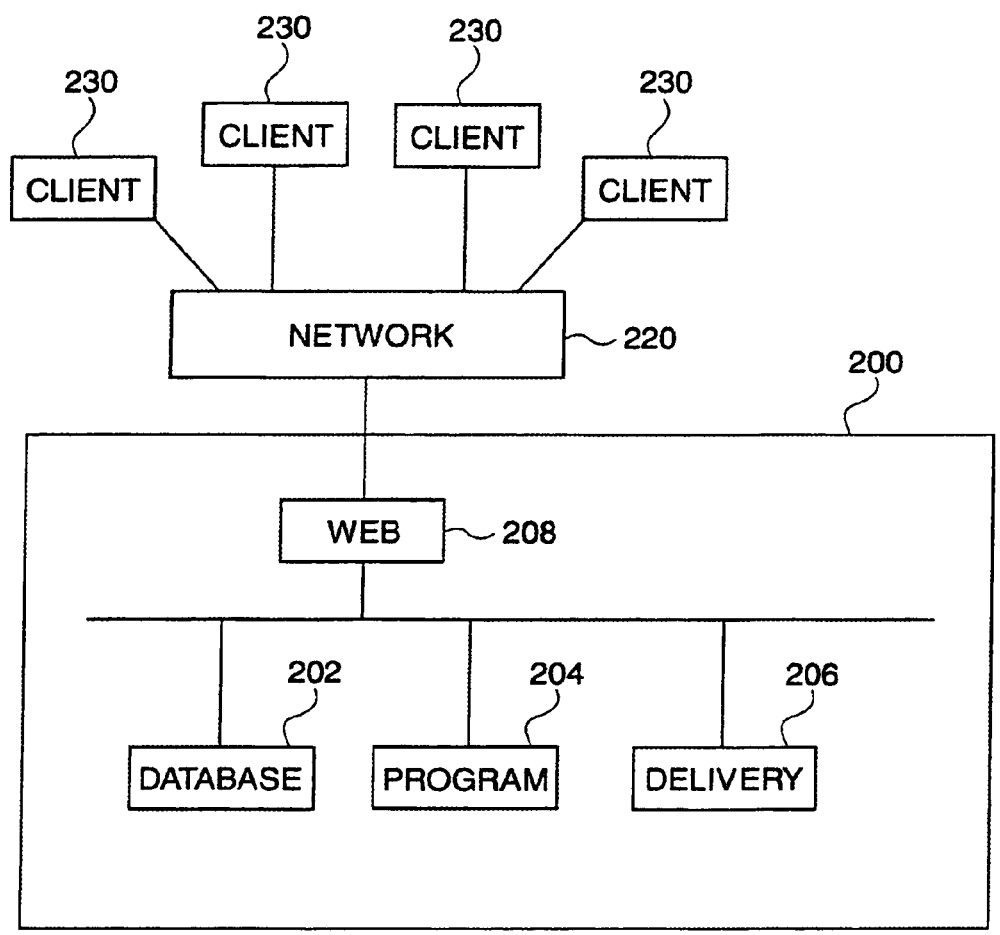
FIG. 1 is a block diagram of an information delivery system which is one preferred embodiment of the present invention.

FIG. 1 is a block diagram of an information delivery system 200 which is one preferred embodiment of the present invention. Referring to FIG. 1, the information delivery system 200 includes a database server 202, a program server 204, a delivery server 206 and a web server 208. These severs 202, 204, 206 and 208 can be constituted by either a single computer or a plurality of computers which are connected by a communication cable(s). The database server 202 includes an information database or storage means (not shown in FIGs.) which stores data or information which is processed or managed by the system 200, as well as users' personal data and requests inputted by the users. The database server 202 manages predetermined information and personal data including their changes made by users, which are stored in the information database. The Program server 204 performs data processing, according to programs stored therein, on various data or information stored in the database server 202 based on personal data inputted by users, and provides information (hereinafter referred to as "personalized information") which will be delivered to users. The delivery server 206 manages incoming and outgoing electronic mails (hereinafter referred to as "e-mails") and data transferred by users. It receives e-mails and data, and interfaces with the database server 202 to store and/or change data. It also schedules and sends outgoing e-mails. It also interfaces with the program server 204 and the database server 202. The web server 208 functions as a network interface which connects the system 200 with client devices 230 through a computer network 220.

The client devices 230 typically include an input means (e.g., a key board or touch keys) for inputting personal data or requests to be sent to the system 200, and an output means (e.g., a printer, a display (e.g., a CRT), and/or a speaker) for providing information transferred from the system 200 to the user. Preferably, the client devices 230 include a computer chip. In a preferred embodiment, the computer network is the Internet and/or a mobile phone network (e.g., i-mode®). Thus, depending on the network used by users and/or their preferences, the clients devices 230 can be a desktop computer, a laptop computer, a portable computer, a mobile phone, a wristwatch, a personal digital assistant (PDA), or the like.

In the preferred embodiment shown in FIG. 1, the information delivery system 200 is connected to the computer network 220 and provides information to users therethrough. Alternatively, the information delivery system 200 can be in the form of a stand-alone computer which is not connected to any computer network but provides information only through an output means which is provided on the information delivery system 200. Such output means preferably includes a printer, a display (e.g., a CRT), and/or a speaker.

Figure 2:
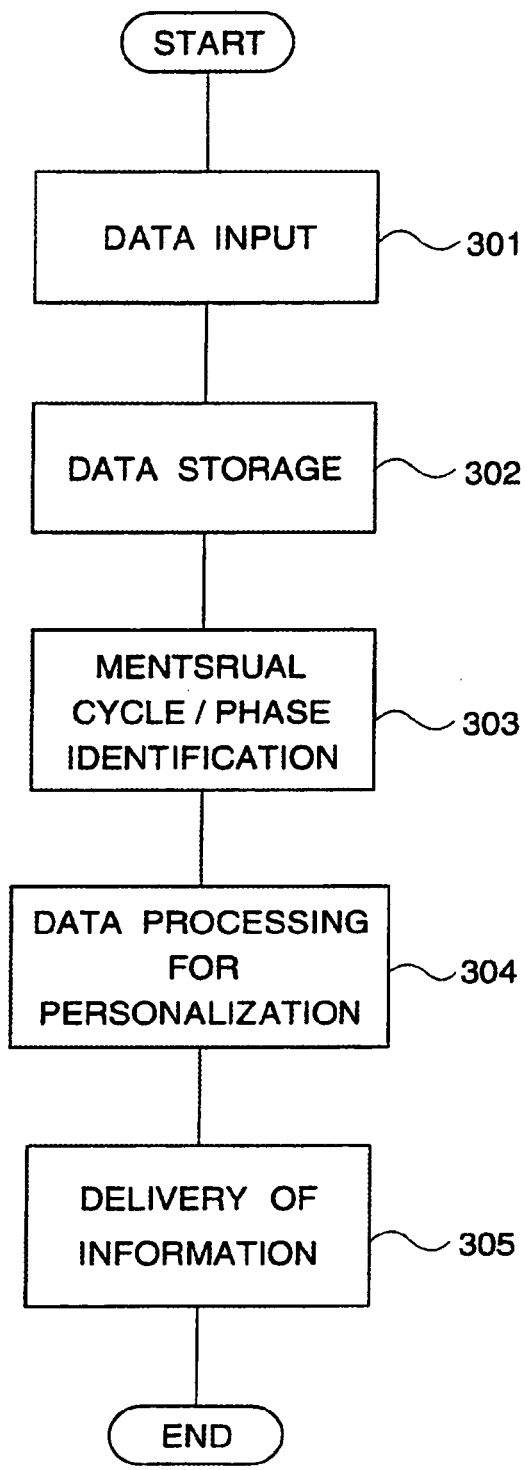
FIG. 2 is a flow chart which generally shows the operation of the information delivery system shown in FIG. 1.

FIG. 2 is a flow chart which generally shows the operation of the information delivery system 200 shown in FIG. 1.

In the step 301, a user enters personal data on a woman (who is typically same as the user). The personal data include profile data and menstrual data. The profile data include the woman's name, the e-mail address, the age, the weight, the height, the underwear size, the pregnancy history, the race, the nationality, the occupation, the interests, the hobbies, and the like. The menstrual data include the menstrual cycle data, the amount of menstrual flow, the menstrual product(s) normally used, the number of the menstrual product(s) normally used in the menstruation phase, the experience in soiling, the regularity of the past menstrual cycles, the pregnancy history, and the like. The menstrual cycle data include at least the first date of the menstruation phase in the current menstrual cycle, the first date of the menstruation phase in the previous menstrual cycle, and the average duration for the menstruation phase. Preferably, the menstrual cycle data further include the dates of the phases in the current menstrual cycle, the dates of the phases in the past menstrual cycle(s), and the duration of each phase in the menstrual cycle.

As is generally known, women sometimes experience changes in the duration of their menstrual cycle. It is also known that some women have irregular menstrual cycles. For example, a woman who normally has a menstrual cycle for 28 days may have a change to 30 days. In another example, a woman who has 5 days for her normal menstruation phase may have a change to 3 days. In a preferred embodiment, these changes in the menstrual cycle is taken into account by the system. In order to do so, a modification procedure for the menstrual data is provided in the system which is called "adjustment procedure". This adjustment procedure can be done through an e-mail, a web site or other communication means known in the art (e.g., a telephone). Preferably, the adjustment procedure is done by users' visiting the web site. This is preferred because users are given an opportunity to access to latest information provided at the web site. Such latest information may be any information which is beneficial to users such as information about new products, information about appropriate products' usage, and the like.

All personal data which are already entered by a user can be modified by the same person through the adjustment procedure which is in this step 301. After the adjustment procedure, the system operates based on the modified data to deliver information.

The user can also enter requests on when or what timing(s), and how or what manner(s) she/he wants to receive information from the system 200 (hereinafter referred to as "delivery requests") at this step 301. For example, if the user wants to receive information immediately, it is requested at this step 301. The delivery requests and the effects thereof will be described in detail hereinafter.

In the step 302, the personal data and the delivery requests are transmitted to the system 200 through the network 220 and are stored therein. More specifically, the database server 202 receives and stores the personal data and the delivery requests which are received through the web server 208.

In the step 303, the program server 204 identifies the woman's current and future menstruation phases and cycles as well as significant menstrual days and dates thereof. The identification is performed based on the menstrual data contained in the personal data. The identification can be performed according to any algorithm known in the art. A preferred process (or algorithm) for the identification will be described in detail hereinafter. The resultant data or information is also stored in the database server 202.

In the step 304, the program server 204 performs data processing on data or information stored in the information database based on the personal data to provide personalized information which will be delivered to the user. The data processing includes at least means for selecting information from the database server 202 or the storage means, and/or means for generating information which defines at least a phase of the menstrual cycle. The data processing for the personalization will be described in detail hereinafter. The personalized information is also stored in the database server 202.

In the step 305, the delivery server 206 sends the personalized information to at least on of the client devices 230 which is designated based on the user's delivery requests. If the delivery requests shows that the user wants to receive information immediately, the delivery server 206 sends out the personalized information immediately. In contrast, if the delivery requests shows that the user wants to receive the personalized information at a certain designated (or desired) timing, the delivery server 206 follows the request. In a preferred embodiment, such a certain designated (or desired) timing is in response to the phase(s) in menstrual cycles identified by the program server 204. Breaking the predetermined information into pieces which are appropriately divided and timely delivering them to users, helps the users or the women to easily learn the information and manage the their lives.

The normal reproductive years of women are characterized by monthly rhythmic changes in the rates of secretion of the female hormones and corresponding changes in the ovaries and sexual organs as well as other parts of women's mental and physical health. This rhythmic pattern is generally known and called as "menstrual cycle". It is also generally known that the average duration for one menstrual cycle is about 28 days, although it is very personal and may change within the range of from about 14 days to about 36 days depending on the person. In a preferred embodiment, the menstrual cycle is considered to be divided into five phases which are: "menstruation", "pre-ovulation", "ovulation", "post-ovulation", and "pre-menstruation". However, in other embodiments, the menstrual cycle can be considered to be divided into less than or more than the five phases. For example, it can be considered to include two phases such as the menstruation phase and the ovulation phase. Alternatively, it can be considered to include three phases such as the menstruation phase, the ovulation phase and the pre-menstruation phase. These phases in the menstrual cycle are characterized by the levels of the female hormones, and their effects on the body and mind of women.

There are five kinds of female hormones which primarily govern the woman's body and mental conditions within the menstrual cycle, i.e., Estrogen hormone (ESH), Progestrone hormone (PGH), Lutenizing hormone Releasing Hormone (LHRH), Follicle Stimulating hormone (FSH), and Lutenizing hormone (LH). The Estrogen hormone is responsible for regulating and sustaining female sexual development and reproductive function. The Progestrone hormone is responsible for preparing the body for the conception of a baby. The Lutenizing Releasing hormone is responsible for releasing Lutenizing hormone. The Follicle Stimulating hormone is responsible for stimulating the ovaries. The Lutenizing hormone is responsible for stimulating the ovulation.

Figure 3:
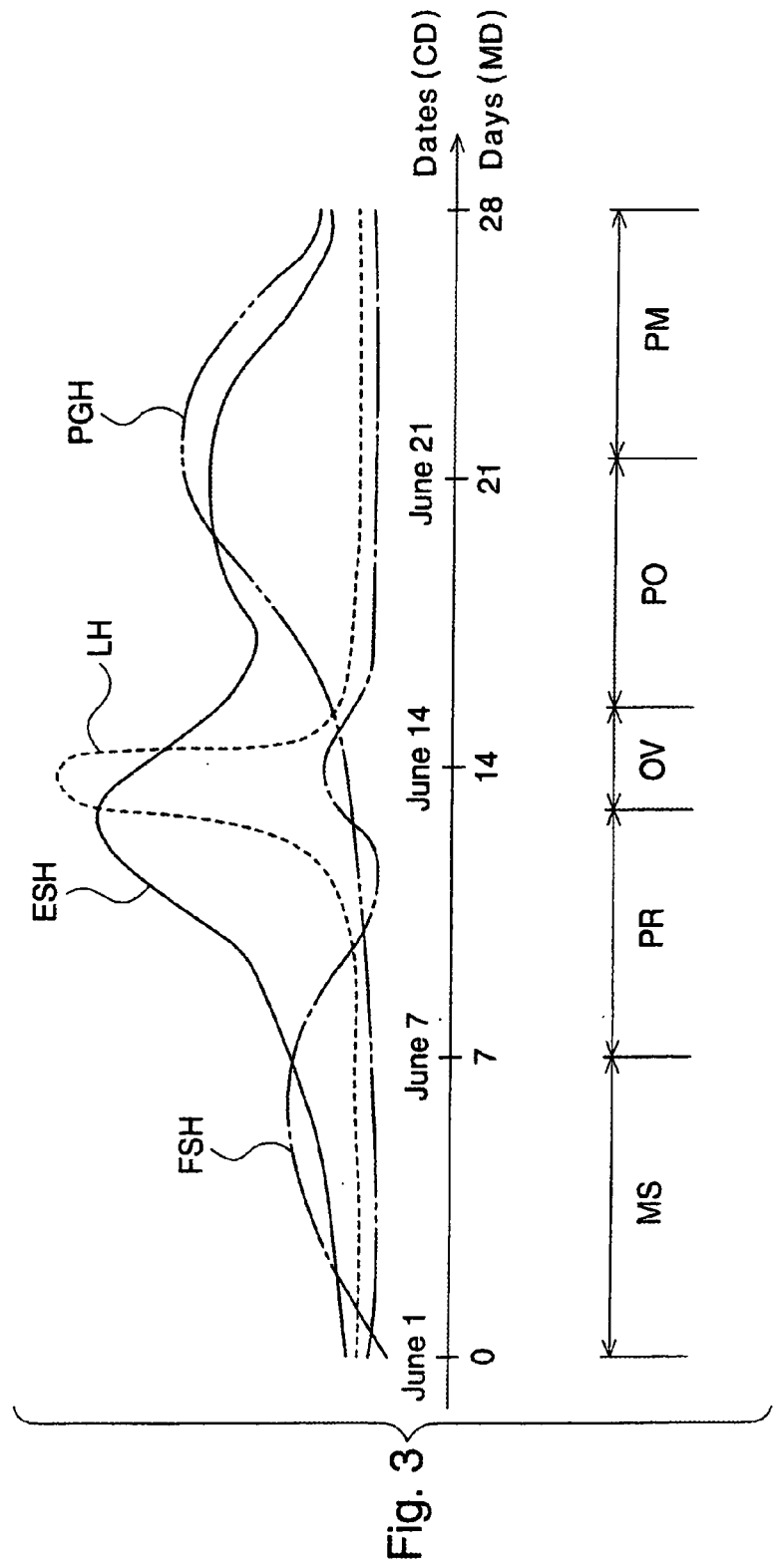
FIG. 3 is a biorhythm chart of 28 days' menstrual cycle of a woman.

FIG. 3 is a biorhythm chart of a typical woman. In FIG. 3, it is assumed that the woman has 28 days in her menstrual cycle. The changes of respective hormone levels are shown by the curves ESH, PGH, FSH and LH in FIG. 3.

In the embodiment shown in FIG. 3, the menstrual cycle is considered to have the following five phases: the menstruation phase (MS), the pre-ovulation phase (PR), the ovulation phase (OV), the post-ovulation phase (PO), and the pre-menstruation phase (PM). While the number of the days for the menstruation phase and the pre-ovulation phase are variable, the numbers for the days for the ovulation phase, the post ovulation phase and the pre-menstruation phase are constant.

The menstruation is the phase of discharging of blood and dead cell debris from the uterus through the vagina by women at approximately monthly intervals between puberty and menopause. Right before menstruation, the estrogen and progestrone levels drop and the Follicle Stimulating hormone is released from the pituitary gland. The falling progesterone causes the endometrium to break and menstruation begins. The menstruation is the flow of blood rich fluid from the vagina. Also, a few of the eggs in the ovaries start to mature. This phase is generally between Day 1 to Day 7 in the 28 days' menstrual cycle.

After the menstruation phase is complete, the pre-ovulation phase begins. The pre-ovulation is the phase in which the body is preparing for ovulation. During the pre-ovulation phase, the egg grows and matures, and the ovary produces high quantities of estrogen. When the estrogen reaches some "high" level, the body stimulates the Lutenizing hormone to trigger the ovulation. This phase is generally between Day 8 to Day 14 in the 28 days' menstrual cycle.

The ovulation is the phase in which the mature egg is released from follicle the ovary. The high level of the estrogen prepares the body for conception. This phase is generally between Day 13 to Day 15 in the 28 days' menstrual cycle. Although the Ovulation phase is sometimes a one day or less than one day event, it is considered as a three days' phase.

The post-ovulation is the phase after the ovulation in which the body is ready to receive a fertilized egg. This phase is generally between Day 15 to Day 21 in the 28 days' menstrual cycle.

The pre-menstruation is the phase after the post-ovulation phase and before the menstruation. Women tends to experience PMS. This phase is generally between Day 22 to Day 28 in the 28 days' menstrual cycle. If the egg is not fertilized, it disintegrates, and the estrogen and progestrone levels become low. The lining of the uterus breaks apart and menstruation occurs.

Assuming that a woman is currently in the n-th menstrual cycle CY(n), the menstrual cycle data which are inputted by a user include the first date of the menstruation phase MSF(n) in the current menstrual cycle CY(n), the first date of the menstruation phase MSF(n) in the previous menstrual cycle CY(n−1), and the average duration AM for the menstruation phase. Based on the menstrual data, the system identifies her days and dates in the current and future menstrual cycles by the following data processing (or calculation). The resultant data or information includes days and dates of the menstrual cycles, days and dates of each phase in the menstrual cycles, and other significant days or dates in the menstrual cycles.

FIG. 4 is a cycle chart of succeeding three menstrual cycles CY(n−1), CY(n) and CY(n+1) of a woman. As indicated in FIG. 4, it is assumed that today is some day in the cycle CY(n). Each cycle CY(n−1), CY(n) and CY(n+1) has the menstruation phase MS, the pre-ovulation phase PR, the ovulation phase OV, the post-ovulation phase PO, and the pre-menstruation phase PM.

Based on the menstrual cycle data MSF(n), MSF(n−1) and AM inputted by a user, the system 200 calculates the cycle length CL, and the first day for the menstruation phase MSF (n+1) in the next cycle CY(n+1), by the following numerical formulas:

$$CL=MSF(n)-MSF(n-1) \quad (1)$$

$$MSF(n+1)=FD(n)+CL \quad (2)$$

The first day for the pre-menstruation phase PMF(n) in the current cycle CY(n) is obtained by the following numerical formula:

$$PMF(n)=MSF(n+1)-7 \quad (3)$$

The first day for the post-ovulation phase POF(n) in the current cycle CY(n) is obtained by the following numerical formula:

$$POF(n)=PMF(n)-7 \quad (4)$$

The first day for the ovulation phase OVF(n) in the current cycle CY(n) is obtained by the following numerical formula:

$$OVF(n)=POF(n)-2 \quad (5)$$

The first day for the pre-ovulation phase PRF(n) in the current cycle CY(n) is obtained by the following numerical formula:

$$PRF(n)=MSF(n)+AM+1 \quad (6)$$

The last days for the respective phases are simply obtained as one day before the first day of the succeeding phases. As a result, all days and dates for the all phases in the current menstrual cycle CY(n) are obtained. Similarly, all future days and dates of the phases in future menstrual cycles CY(n+1, 2, ...) can be obtained or identified.

In an example wherein the first date of the menstruation phase MSF(n) in the current menstrual cycle CY(n) is May 1; the first date of the menstruation phase MSF(n) in the previous menstrual cycle CY(n−1) is April 1; and the average duration AM for the menstruation phase is 5 days. The system calculates by the formula (1) the cycle length CL which is 30 days. The system also calculates by the formula (2) the first day for the menstruation phase MSF(n+1) in the next cycle CY(n+1) which is May 31. The system further calculates by the formula (3) the first day for the pre-menstruation phase PMF(n) in the current cycle CY(n) which is May 24. The system further calculates by the formula (4) the first day for the post-ovulation phase POF(n) in the current cycle CY(n) which is May 17. The system further calculates by the formula (5) the first day for the ovulation phase OVF(n) in the current cycle CY(n) which is May 15. The system further calculates by the formula (6) the first day for the pre-ovulation phase PRF(n) in the current cycle CY(n) which is May 6. As a result, the system obtain the following dates: May 31-June 4 for the menstruation phase of the next menstrual cycle; May 24-May 30 for the pre-menstruation phase; and May 17-May 23 for the post ovulation phase; May 15-May 17 for the ovulation phase. Then system computes dates of the menstruation phase, i.e. May 1-May 5. Then difference between May 15, and May 5 will be calculated as the pre-ovulation phase, i.e. May 6-May 15.

The above calculation is based on the following assumptions: (a) The total length for one menstrual cycle is the sum of the number of the days of the phases for the menstruation, the pre-ovulation, the ovulation, the post ovulation and the pre-menstruation. (b) The total number of the days for the post-ovulation phase and the pre-menstruation phase is 14 days. For the sake of calculation, the post-ovulation phase is fixed for 7 days, and the pre-menstruation phase is fixed for 7 days. (c) The ovulation phase is fixed for 3 days. One day overlaps with the pre-menstruation phase, and another one day with the post-ovulation phase. The ovulation is likely to happen on the second day of the 3 day phase. (d) The number of days in the menstruation and pre-ovulation phases are variable. (e) The total length for one menstrual cycle is 28 day, unless different data is provided.

The future phases and menstrual cycles decided by the above described manner are merely a prediction, i.e., there is a possibility of changes from the prediction. Preferably, the possibility of such changes is taken into account by the system for a more accurate prediction based on the user's modification to the menstrual data which are previously inputted, the history in the past menstrual cycles, and other menstrual related data.

The personalized information is selected by the system 200 by selectively retrieving information from the information database which is provided in the database server 202 shown in FIG. 1. The information database contains a variety of information which is thought as being valuable to the users to know. The predetermined information in the information database can be classified according the phases of the menstrual cycle (hereinafter referred to as "phase classified information"), and at least some of the profile data in the personal data (hereinafter referred to as "profile classified information"). The classification of the predetermined information is made by adding retrieval terms to respective information. The phase classified information includes physical information, mental information, activity information, and lifestyle information. The profile classified information includes information related to age, menstrual flow, product type, weight/height, and the like. The personalized information is chosen from the information database by the system based on the profile data and the menstrual data.

The physical information includes any information which is related to a woman's body. The physical information includes human biological system information which explains possible and known body condition. Examples of biological system information include reproductive system information, digestive system information, urinary system information, endocrine system information, circulatory system information, nervous system information, and the like.

The mental information includes any information which relates to a woman's mind. The mental information includes emotional information, information, metaphysical information, and spiritual information. The Emotional information is information which relates to a person's feeling or mood. The spiritual information is information which relates to sacred and/or religious matters. The metaphysical information includes fictional, fantasy, hunch, instinct, supernatural, and paranormal matters.

The phase change in the menstrual cycle tends to influence the woman's mental condition. For example, during the pre-menstruation and menstruation phases, the estrogen and progestrone levels drop in the woman's body. The low level of estrogen decreases the production of serotonin which leads to alteration in moods. At the pre-menstruation and/or menstruation phases, a woman tends to become more sensitive and emotional. Based on these facts, the personalized advice which is preliminary prepared and stored in the storage means tries to inform a woman of the physical condition where she is currently in, and/or provide advice for dealing with any rising issues. For example, if a woman is identified to be in the menstruation phase, she is advised having an aroma therapy treatment to relax herself and focus internally. Such advice is chosen from the information database stored in the storage means of the system.

The activity information is any information which is related to a woman's activities. The activity information includes periodic (e.g., daily, weekly and monthly) activity information, diet activity information, health activity information, physical appearance information, physical fitness information, diagnostic information, and the like. Periodic activity means activity which needs to be performed on a regular interval. For example, self breast examination is an activity which should be regularly performed at the pre-ovulation phase every menstrual cycle. Diet activity can be defined as activity which relates to the food and drink intake of a person. For example, women can take Vitamin B6 to cope up with vitamin deficiencies associated with PMS symptoms. The health information includes information related to conditions of body and mind. The physical appearance includes information related to the outward look of a person. The fitness information is information related to improve the physical condition of the body. For example, if a woman is in the pre-ovulation phase, she is recommended to do strenuous exercise because her energy levels are high during this phase. In another example, if a woman is in the post-ovulation phase, she is recommended to eat chocolates since chocolates have a high amount of magnesium which is needed to metabolize the estrogen produced. In an yet another example, if a woman is in the pre-ovulation phase, she is recommended to drink some green tea to balance the fluid levels in their bodies. In a still another example, if a woman is in the ovulation phase, she tends to look and feel the best. During this phase, she is recommended to be aware of her appearance and use the opportunity to increase the self esteem. In an yet another example, if a woman is in the menstruation phase, she is advised to take iron supplements to make up for the loss of blood through menstruation.

The lifestyle information is information which helps a woman to manage her menstrual cycle better. The lifestyle information in turn can improve her everyday life and lifestyle. The lifestyle information includes information related to life stage, menstrual pain or discomfort, beauty, self confidence, self esteem, relationship and horoscopes. For example, when a woman is in menopause, she tends to have feelings of loss or decreased femininity. Thus, the information to be provided for her preferably includes advice which tries to increase her self esteem and to deal with aging. In another example, if a woman is in the pre-ovulation phase, she tends to have good moods and is known to be more sociable. The information to be provided for her is to concentrate on building her relationship with her spouse, relatives and friends. In an yet another example, if a woman is in the post-ovulation, she tends to suffer from increased skin oiliness. The information to be provided for her is to prevent acne from her face by washing her face frequently.

The profile classified information includes information related to age, menstrual flow, product type, weight/height, and the like. Age information is classified into several age groups. Women's menstrual cycle, physical and mental attributes change with age. For example, when a woman is in menopause, she tends to have feelings of loss or decreased femininity. Thus, the information to be provided for her preferably includes advice which tries to increase her self esteem and to deal with aging. The menstrual flow information is classified into heavy, medium or light. Different information can be provided based on the woman's menstrual flow. For example, a woman who has a heavy flow can be cautioned to purchase a sanitary napkin(s) which is particularly designed for heavy flow to provide a better protection against soiling. The product type information is classified into pads and tampons. For example, a woman who is a tampon user, the product type information classified by the tampon includes a caution that tampons need to be changed every 8 hours. The weight/height information is used to advice menstrual product, diet, physical information to women. For example, a woman who has relatively greater weight and height, the weight/height information includes an advice that a sanitary napkin(s) which is long is recommended.

The Table I shows a preferred structure of the predetermined information.

TABLE I

| No. | Predetermined Information | RT1 | RT2 | ... | RTm |
|---|---|---|---|---|---|
| 1 | PI(1) | RT1(1) | RT2(1) | ... | RTm(1) |
| 2 | PI(2) | RT1(2) | RT2(2) | ... | RTm(2) |
| . | . | . | . | ... | . |
| . | . | . | . |  | . |
| . | . | . | . |  | . |
| N | PI(N) | RT1(N) | RT2(N) | ... | RTm(N) |

As shown in the Table I, the predetermined information has a structure of a matrix wherein each information PI(1)-PI(N) has retrieval terms RT1-RTm which are used for the retrieval operation. In other words, the predetermined information PI(1)-PI(N) are classified with attributes which correspond to the retrieval terms RT1-RTm. Most of the attributes which are inputted by users as the personal data can be used for the retrieval terms RT1-RTm. Preferred retrieval terms or attributes include the age, the weight, the height, the underwear size, the pregnancy history, the race, the nationality, the occupation, the interests, the hobbies, the amount of menstrual flow, the menstrual product(s) normally used, the number of the menstrual product(s) normally used in the menstruation phase, the experience in soiling, the regularity of the past menstrual cycles, the pregnancy history, and the duration of each phase in the menstrual cycle. The total number m of the retrieval terms is at least 10, preferably at least 20, and more preferably at least 40. The greater number for the total number m is more preferred, since more appropriate information can be retrieved from the predetermined information PI(1)-PI(N).

Preferably, the total number N of the predetermined information which can be retrieved individually is at least 1,000, and more preferably at least 10,000. The greater number is more preferred for the total number N, since more appropriate information can be retrieved from the predetermined information PI(1)-PI(N).

The retrieval terms RT1-RTm are used by the system to retrieve information which will be sent as the personalized information. The retrieval term RT1-RTm correspond to the respective attributes which are used to retrieve information from the predetermined information IP(1)-IP(N). For example, the terms RT1-RTm correspond to the following attributes, respectively: the age or the age range, the phase in the menstrual cycle, the flow level, and the type of the phase classified information (i.e., the physical information, the mental information, the activity information, and the lifestyle information). An example of the structure which has such attributes is shown in the Table II.

TABLE II

| No. | Predetermined Information | Age | Phase | Flow | Type |
|---|---|---|---|---|---|
| 1 | If you want to get pregnant, this is the right time for conceiving. | 19–24, 25–29, 30–34, | OV | Light, Medium, Heavy | Physical |
| 2 | This is good time for doing a self breast examination. The latest news from the American Cancer Society is . . . | 15–19, 20–24, 25–29, 30–34, 35–39, 40 and over | PR | Light, Medium, Heavy | Activity, Lifestyle |
| 3 | Does everyone's head looks like an invitation to batting practice? You may be suffering from PMS. We advise you concentrate on your inner self by meditation. | 15–19, 20–24 | PM | Light, Medium, Heavy | Mental, Lifestyle |
| 4 | Give into your temptation for chocolates. You need that Magnesium, that is in chocolates. | 10–15, 16–19, 19–24, 25–29, 30–34, 35–39, 40 and over | PO | Light, Medium, Heavy | Activity |
| 5 | It is time for you to buy sanitary napkins. Remember to buy the ones especially for "Heavy flow". | 15–19, 19–24, 25–29, 30–34, 35–39 | PM | Heavy | Activity, Physical |
| 6 | Do you see pimples again? Control the oiliness on your face with frequent rinsing. | 10–15, 15–19, | PM | Light, Medium, Heavy | Activity, Lifestyle |

In this example, the retrieval term for age includes the following age groups: less than 10, 10-15, 16-19, 20-24, 25-29, 30-34, 35-39, 40-44, and 45 and above. The retrieval term for the phase includes the following phases: the menstruation phase (MS), the pre-ovulation phase (PR), the ovulation phase (OV), the post-ovulation phase (PO), and the pre-menstruation phase (PM). The retrieval term for the flow includes the following flow levels: light, medium, and heavy. The retrieval term for the type includes the following types of information: the physical information, the mental information, the activity information, and the lifestyle information.

A preferred means for selecting information from the predetermined information is a data processing operation for data retrieval on the predetermined information. Preferably, the selection means selects the information based on the menstrual data or the profile data. The retrieval of the predetermined information can be done by using any retrieval terms RT1-RTm. In a preferred embodiment, the phase which was identified by the system is used as a retrieval term for the first retrieval operation. Preferably, a plurality of hits (e.g., more than 10 hits) are obtained by one retrieval operation. The system preferably selects one information by repeating a retrieval operation(s) by using a different retrieval term from that which has already been used in the previous retrieval. To repeat such retrieval operations, the retrieval terms RT1-RTm preferably have levels of priorities which show the order of the retrieval terms to be used for the retrieval. Such levels of priorities for the retrieval terms can be determined by the system or designated by the users. In a preferred embodiment, levels of priorities for the retrieval terms are designated by a user through the delivery request procedure. In an alternative preferred embodiment, the system can select one information, among the plurality of hits, by a random selection wherein one information is chosen at will by the system. Preferably, the system keeps a record on what information was already sent to the user. Based on the record, the system avoids sending the same information repeatedly to the same user within a short time period (e.g., 6 months).

In the example of Table II, assuming the personal data shown in Table III are inputted by a user, the retrieval operations are performed as the follows.

TABLE III

| Name | Mary Jones |
|---|---|
| Age | 22 |
| Menstrual Cycle Dates | Jun. 1, 2000 (the beginning of the last menstruation phase) |
| Menstrual Flow | Heavy |
| . | . |
| . | . |
| . | . |
| Past Information | Information Nos. 1, 2, 3, 6 |

The first retrieval operation is performed by considering the numbers of the predetermined information which were already sent to the same person. Since the numbers 1, 2, 3 and 6 of the predetermined information were already sent in this example, the rest of the numbers 4 and 5 of the predetermined information are left for a further retrieval operation(s). The system then performs the second retrieval operation by using the phase identified. Assuming the system identifies the next phase of the woman as the pre-menstruation (PM), the second retrieval operation is performed by using the pre-menstruation (PM). As a result, the number 5 of the predetermined information is retrieved. This information will be sent to the user as the personalized information.

A woman has about 400 menstrual cycles on average in her lifetime. In a preferred embodiment, the system is designed to periodically provide or deliver personalized information roughly for these 400 (or more) menstrual cycles. Breaking the predetermined information or already known information into pieces which are appropriately divided and timely delivering them to the user, helps the user or the woman to easily learn the information and manage her life.

The personalized information includes menstrual cycle information and recommendation information. The menstrual cycle information is the information about when (i.e., what dates) a woman moves to what phase in her menstrual cycles. The menstrual cycle information includes at least significant dates for the menstruation, i.e., the first day for the menstruation phase in the menstrual cycle. The menstrual cycle information preferably includes such information both for the future and the past. More preferably, the menstrual cycle information further includes the length and dates (i.e., the duration) for the menstruation phase, the pre-ovulation phase, the ovulation phase, the post-ovulation phase, and/or the pre-menstruation phase. In a preferred embodiment, the menstrual cycle information includes a biorhythm chart which shows any biorhythmic change of a woman's body. A preferred example of the biorhythm chart is shown in FIG. 3. As shown in FIG. 3, the biorhythm chart shows a level change(s) of at least one, preferably all of the five hormones in the menstrual cycles, i.e., Estrogen hormone (ESH), Progestrone hormone (PGH), Lutenizing hormone Releasing Hormone (LHRH), Follicle Stimulating hormone (FSH), and Lutenizing hormone (LH).

In a preferred embodiment, the system includes means for generating information which defines at least a phase of the menstrual cycle. Preferably, the information which defines at least a phase of the menstrual cycle (hereinafter referred to as "phase related information") is at least two dates which are in the menstrual cycle. Such two dates can be chosen from the all dates in the menstrual cycle. Preferably, the at least two dates include the first day for the menstruation phase and the first day for the ovulation phase. Alternatively, the phase related information may be one day which is chosen from the dates which are in the pre-ovulation phase, the ovulation phase, the post-ovulation phase, and the pre-menstruation phase. The phase related information can be any form as long as it shows at least the menstrual dates in the calendar dates CD or the menstrual days in the menstrual cycle days MD which are shown in FIG. 3 as an example.

In an alternative preferred embodiment, the phase related information includes information which is combined with a phase identified by the system. In a more preferred embodiment, the phase related information is a biorhythm chart which is combined with a phase identified by the system. FIG. 3 shows a preferred example of such a biorhythm chart.

The recommendation information is the information which is retrieved from the predetermined information by the retrieval operation(s) and is delivered to users as recommendation.

The delivery of the personalized information from the system can be made any communication manner known in the art. Preferably, the delivery manner is chosen by the user at the data input step 301 shown in FIG. 2. In a preferred embodiment, the delivery manner is an e-mail. The e-mail address is also inputted by the user at the data input step 301. In an alternative preferred invention, the delivery of information is performed on the web site, e.g., the personalized information is indicated on a web site. If it is preferred by the user, a letter which describes the personalized information may be sent to the user by the postal mail or a facsimile.

The personalized information can be indicated in any format. Preferably, the indication format is chosen by the user at the data input step 301 shown in FIG. 2. In a preferred embodiment, the personalized information can be indicated in a text format or a web enabled format. Preferred web enabled formats include Hyper Text Markup Language (HTML) format, Compact Hyper Text Mark-up Language (CHTML) format, Extensible Markup Language format (XML), Handheld Device Markup Language (HDML) format, and the like. Preferred forms for the personalized information to be indicated include plain text, link addresses, graphics, pictures, tables, links, lists, and the like. In a preferred embodiment, the menstrual cycle information is provided in a graphic or a picture such as a calendar format wherein all phases of the menstrual cycle are marked in a calendar. Similarly, the format for the indication of the recommendation information is decided by the system, or chosen by the user if appropriate, depending on the contents of the information to be delivered.

The timing(s) for the delivery of personalized information from the system to users in response to the phase identified by the system can be determined by the system, or preferably be designated by users. In response to the phase identified by the system, the system delivers the personalized information to users according to the timing(s). Preferably, the timing(s) for delivery is chosen by the user at the data input step 301 shown in FIG. 2. A preferred timing for the delivery is an automatic time interval, for example, a few days (e.g., 1-3 days) before the beginning of every menstruation phase. In a preferred embodiment, the timing for delivery is designated at one day before the first day of the menstruation phase, the last day of the menstruation phase, the first day of the ovulation phase, the last day of the ovulation phase, the first day of the pre-menstruation phase, and/or the last day of the pre-menstruation phase. For example, the system delivers the personalized information one day before the beginning of the menstruation phase, and thereafter delivers the personalized information after 28 days if no adjustment is requested. The timing for delivery may be preliminarily decided by the system, although it can be preferably changed by users. In a preferred embodiment, the frequency and/or numbers of delivery of the personalized information in one menstrual cycle can be designated or requested by users.

In a preferred embodiment, the user can request the delivery of information immediately or instantly (hereinafter referred to as "instant advice"). The instant advice can be given to the user through an e-mail or on the web site (or the postal mail or a facsimile if desired). After a user send an e-mail to the system with their personal data as well as the request for the instant advice, the system process the request. Upon completing the data processing, the system delivers the personalized information by an e-mail instantly. Alternatively, the user can enter the personal data and click a button for the instant advice on the web site. The system provides the personalized information on the web site in response to the request instantly.

It is understood that the examples and embodiments described herein are for illustrative purpose only and that various modifications or changes will be suggested to one skilled in the art without departing from the scope of the present invention.

What is claimed is:

1. A system for delivering information comprising:
a client device for collecting personal data including menstrual data regarding a menstrual cycle on a woman from a user;
a database server for storing predetermined information;
a program server for selecting information from the predetermined information stored on the database server, and for identifying a phase within the menstrual cycle based on the personal data, and for generating personalized information based on the phase identified; and
a delivery server for delivering the personalized information and the phase related information to the client device,
wherein the predetermined information includes phase classified information which is classified according to the phases of the menstrual cycle, and wherein the phase classified information includes physical information, mental information, activity information, and lifestyle information.

2. The system of claim 1, wherein the personal data further includes profile data on the woman, and the predetermined information further includes profile classified information which is classified according to the profile data in the personal data.

3. The system of claim 1, wherein the phase related information is selected from the pre-ovulation phase, the ovulation phase, the post-ovulation phase, the premenstruation phase, and/or the menstruation phase.

4. The system of claim 1, wherein the computer is a server computer, and the client device includes a computer network which connects the server computer to the client device.

5. The system of claim 4, wherein the client computer is provided in a mobile device.

6. The system of claim 5, wherein the mobile device is a mobile phone, a wristwatch, a mobile computer, or a personal digital assistant (PDA).

7. The system of claim 1, wherein the client device is a mobile device.

8. The system of claim 1, wherein the computer is a stand alone type computer, and the client device includes an output means provided in the stand alone type computer.

9. The system of claim 1, further comprising communication means for modifying the menstrual data which was already collected, based on the user's input.

10. The system of claim 4, wherein the computer network is an Internet or a mobile phone network.

11. The system of claim 1, wherein the information which defines at least a phase of the menstrual cycle includes at least two dates which are in the menstrual cycle.

12. The system of claim 11, wherein the at least two dates include the first day for the menstruation phase and the first day for the ovulation phase.

13. The system of claim 1, wherein the information which defines at least a phase of the menstrual cycle includes information which is combined with the phase identified.

14. The system of claim 13, wherein the information which is combined with a phase is a biorhythm chart.

15. The system of claim 1, further comprising delivery designation means for designating the time, relating to the menstrual cycle, when the user desires to receive the information.

16. The system of claim 1, wherein the system keeps a record of phase classified information and phase related information that has been provided to the user previously.

17. The system of claim 16, wherein the system avoids sending the previously provided information to the user over a short time period.

18. A system for delivering information comprising:
a client device for collecting personal data including menstrual data regarding a menstrual cycle on a woman from a user;
a database server for storing predetermined information;
a program server for selecting information from the predetermined information stored on the database server, and for identifying a phase within the menstrual cycle based on the personal data, and for generating personalized information from the predetermined information based on the phase identified and for selecting product recommendation information that is selected based on the personal data; and
a delivery server for delivering the personalized information and the product recommendation information to the client device,
wherein the menstrual data includes amount of menstrual flow, menstrual product(s) normally used, number of the menstrual product(s) normally used, soiling, or pregnancy history, and the predetermined information includes phase classified information which is classified according to the phases of the menstrual cycle, and wherein the phase classified information includes physical information, mental information, activity information, and lifestyle information.

19. The system of claim 18, wherein the product recommendation information includes product type information.

20. The system of claim 18, wherein the client device is a mobile device.

21. A method for delivering information which is stored in a database server through a computer, comprising the steps of:
- collecting personal data including menstrual data regarding a menstrual cycle on a woman from a user;
- identifying a phase within the menstrual cycle;
- selecting predetermined information, from the database server, which is personalized based on the identified phase; and
- delivering the personalized information by e-mail accessible by the user, to a web page viewable by the user, and/or to a mobile device viewable to the user,
- wherein the predetermined information includes phase classified information which is classified according to the phases of the menstrual cycle, and wherein the phase classified information includes physical information, mental information, activity information, and lifestyle information.

22. The method of claim 21, wherein the method further includes selecting product recommendation information based on the personal data and delivering the product recommendation information to the user.

23. A system for delivering information through a computer, comprising:
- a web server for collecting personal data including menstrual data regarding a menstrual cycle on a woman from a user;
- a database server for storing predetermined information;
- a program server for selecting information from the predetermined information stored on the database server, and for identifying a phase within the menstrual cycle based on the personal data, and for generating personalized information based on the phase identified; and
- a delivery server for delivering the personalized information and the phase related information,
- wherein the predetermined information includes phase classified information which is classified according to the phases of the menstrual cycle, and wherein the phase classified information includes physical information, mental information, activity information, and lifestyle information.

* * * * *